United States Patent
Collura et al.

(10) Patent No.: US 6,574,513 B1
(45) Date of Patent: Jun. 3, 2003

(54) EEG ELECTRODE ASSEMBLIES

(75) Inventors: Thomas F. Collura, Mayfield Hts., OH (US); Joan Gambrill, Chesterland, OH (US); John Collura, Chesterland, OH (US)

(73) Assignee: Brainmaster Technologies, Inc., Mayfield Heights, OH (US)

( * ) Notice: Subject to any disclaimer, the term of this patent is extended or adjusted under 35 U.S.C. 154(b) by 228 days.

(21) Appl. No.: 09/678,348

(22) Filed: Oct. 3, 2000

(51) Int. Cl.⁷ .................................................. A61N 1/04
(52) U.S. Cl. ...................... 607/122; 607/123; 607/383; 600/393; 600/153
(58) Field of Search .................. 600/14, 153, 544–546, 600/300, 383, 386, 391, 393, 396, 397, 372, 139; 607/123, 383, 122

(56) References Cited

U.S. PATENT DOCUMENTS

| | | | |
|---|---|---|---|
| 4,171,696 A | 10/1979 | John | 128/731 |
| 4,537,198 A | * 8/1985 | Corbett | 128/639 |
| 4,683,892 A | * 8/1987 | Johansson et al. | 128/639 |
| 5,357,957 A | * 10/1994 | Itil et al. | 128/644 |
| 5,479,934 A | 1/1996 | Imran | 128/731 |
| 5,511,548 A | 4/1996 | Riazzi et al. | 128/641 |
| 5,630,422 A | 5/1997 | Zanakis | 128/664 |
| 5,730,146 A | 3/1998 | Itil et al. | 128/732 |
| 5,740,812 A | 4/1998 | Cowan | 128/732 |
| 5,800,351 A | 9/1998 | Mann | 600/383 |
| 6,047,202 A | 4/2000 | Finneran et al. | 600/382 |
| 6,067,464 A | 5/2000 | Musha | 600/383 |
| 6,161,030 A | * 12/2000 | Levendowski et al. | 600/383 |

* cited by examiner

Primary Examiner—Tony M. Argenbright
Assistant Examiner—Johnny H. Hoang
(74) Attorney, Agent, or Firm—Arter & Hadden LLP

(57) ABSTRACT

An EEG electrode system for establishing positive electrical contact with the scalp, uses absorptive electrode wrap material in contact with metallic electrodes, with saturated electrode wrap material placed in contact with the scalp. Saturation of the electrode warp material with a conductive solution such as saline provides mechanically and electrically stable contact at multiple scalp electrode sites. An electrode wrap holder assembly holds the electrode wrap and an exposed portion of the electrode wrap in contact with the scalp, while providing access to the electrode wrap for re-wetting with the conductive solution if required. The electrode wrap holders are mounted in straps, hard caps or other headgear. Adjustment of the electrode wrap holders within the mounts further compresses the flexible, absorptive electrode wrap, causing flow of the conductive solution therein and enhancement of the electrical contact.

32 Claims, 4 Drawing Sheets

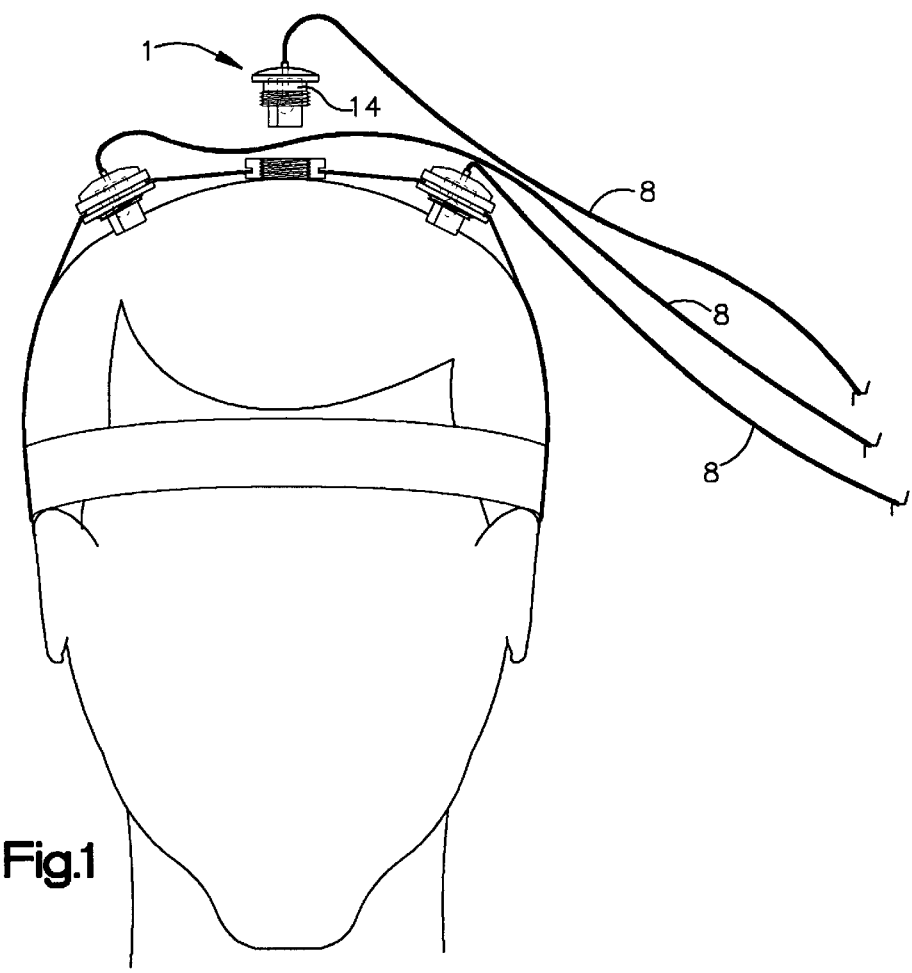
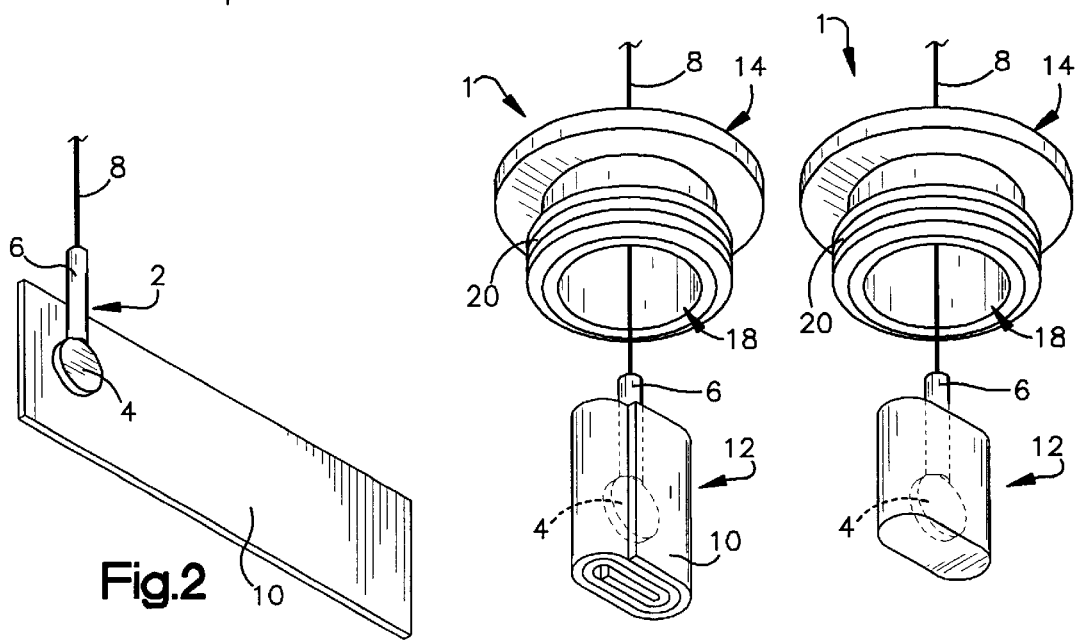
Fig.1
Fig.2
Fig.3A
Fig.3B

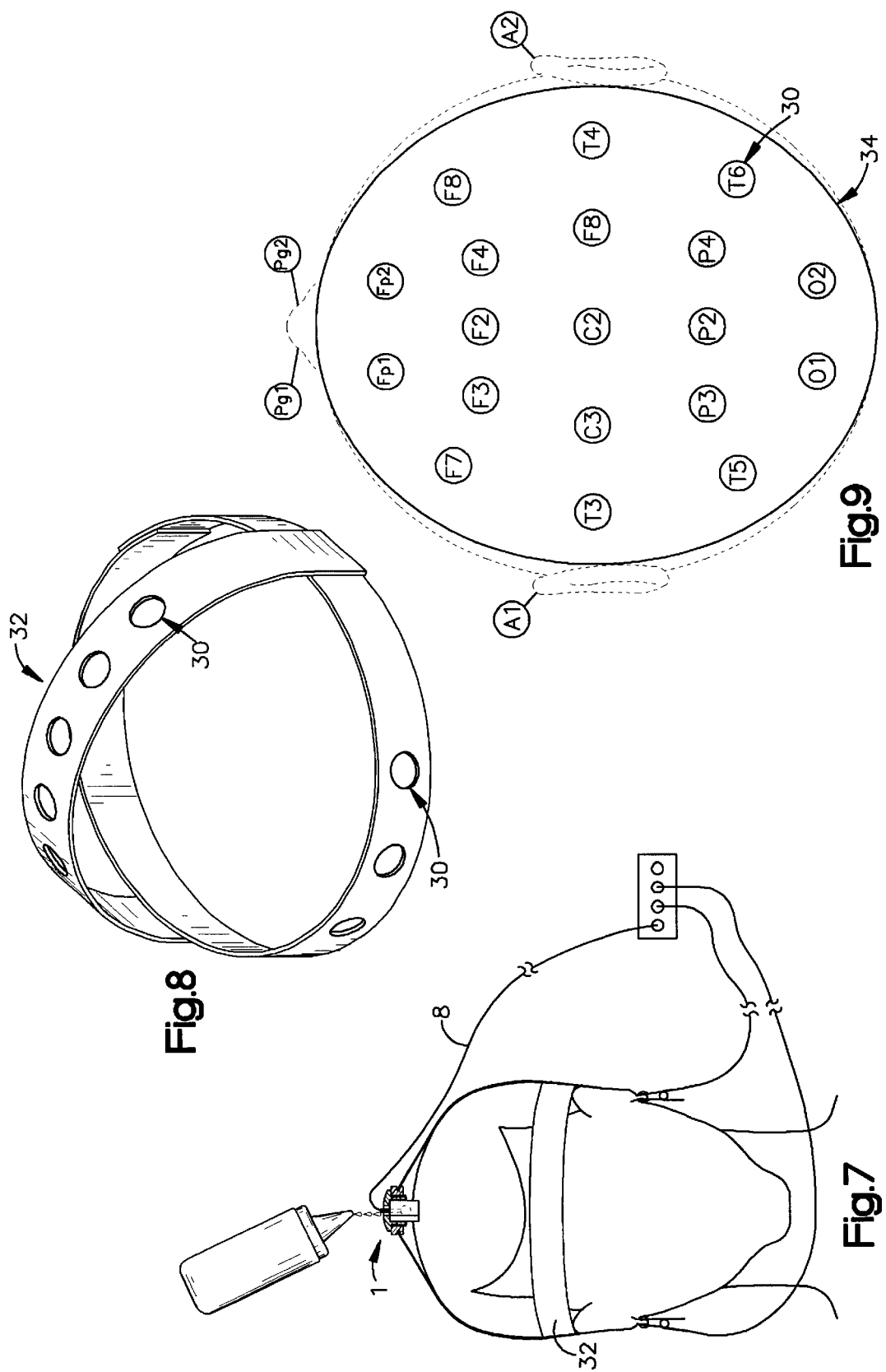

EEG ELECTRODE ASSEMBLIES

FIELD OF THE INVENTION

The present invention relates generally to detection and monitoring of electrical signals generated by the brain and, more particularly, to equipment for electrically connecting human subjects to brain wave detection instrumentation.

BACKGROUND OF THE INVENTION

Electrical energy produced by the brain is detectable by placement of electrodes in conductive low impedance contact with the scalp. Positive connection of each electrode is critical to obtaining valid EEG signals. Hair and dirt on the scalp are the primary impediments to establishing a good electrical contact with an electrode to the scalp. Conventional scalp electrode attachment is very tedious and labor intensive, requiring either hair removal or displacement, scalp cleaning, and in some cases application of a conductive agent such as gel or solution between the electrode and the scalp. Typical clinical EEG analysis requires at least nineteen electrodes to be attached to the scalp, and advanced analysis may require 100 or more electrodes. This is very time consuming and largely impractical for many types of EEG usage such as biofeedback training.

Different systems have been devised to provide quick connection electrode arrays for the scalp. Most of these involve the use of a specialized cap or strapped-on headgear in which electrodes are mounted. The straps support electrode mounting structures at multiple sites. The electrodes are mounted to protrude from the strap mounts in contact with the scalp. Although these types of devices position multiple electrodes next to the head or hair, they do not necessarily establish positive conductive contact of each electrode with the scalp. The contact of each electrode must still be separately established and confirmed throughout the monitoring process.

SUMMARY OF THE INVENTION

The present invention overcomes these and other deficiencies of the prior art, by providing a simple EEG electrode assembly and method which establishes positive conductive contact with the scalp. The invention provides a simple, clean, paste-free and gel-free electrode system for use in EEG, EMG, EKG and related body potential work. The electrode assemblies can be used to establish electrical contact and record biopotentials from the head, face and other body areas. The electrode assemblies are especially advantageous in applications where it is difficult to get a food electrical connection through hair, and where the use of conductive gels or pastes is to be avoided.

In accordance with one general aspect of the invention, there is provided an EEG electrode assembly having an electrode connected to an electrical lead, a fibrous, absorptive and conductive electrode wrapping substantially encompassing the electrode, an electrode holder having an opening for receiving a wrapped electrode, the electrode holder being configured for engagement with a fixture supported by a strap for holding the electrode assembly in contact with a scalp. In one particular embodiment, the electrode holder is a generally cylindrical plug having an internal cylindrical opening for receiving a wrapped electrode, and an engagement structure such as threads on an exterior of the electrode holder for engagement with a corresponding structure in a retaining ring fixture supported by a strap for attachment to a head, in order to place the electrode assembly in positive conductive contact with the scalp. In another aspect of the invention, there are provided multiple electrode holder support structures in different types of head gear such as caps or hats which position the electrode assemblies engaged in the support structures in positive conductive contact with the scalp.

In a particular embodiment of the invention, there is provided an adjustable plastic electrode holder configured to contain an electrode wrapped in a piece of felt, with an electric lead wire extending from the electrode and the felt. The felt is wrapped about the electrode in a rolled manner, and the generally cylindrical felt/electrode assembly fits within a cylindrical cavity in the electrode holder. Male threads are formed on an exterior of the electrode holder, and engaged with female threads in a retaining ring supported by a strap or band or other support structure such as a cap.

In use, the electrode assemblies provide a clean, wet and physically and electrically secure connection to skin by absorption of a conductive saline solution by felt wrapped around the electrode. The absorptive fibrous or fabric electrode wrapping is saturated with a conductive solution to achieve a good electrical connection. Moisture flows from the wrapping to the underlying hair or skin to establish a current path.

These and other aspects of the invention are herein described in detail with reference to the accompanying Figures.

BRIEF DESCRIPTION OF THE FIGURES

FIG. 1 is an assembly view of a wrapped electrode assembly of the invention;

FIG. 2 is a perspective view of a portion of a wrapped electrode assembly of the invention;

FIG. 3 is a perspective view of a portion of a wrapped electrode assembly of the invention;

FIG. 7 is a schematic view of a representative one-channel EEG monitoring using a single scalp-mounted electrode assembly of the invention;

FIG. 8 is a perspective view of a mounting device for positioning and holding wrapped electrodes of the invention on a scalp;

FIG. 9 is top view of an EEG electrode mounting assembly having a plurality of electrodes mounting points within a cap or hat for conductive contact with the scalp.

DETAILED DESCRIPTION OF PREFERRED AND ALTERNATE EMBODIMENTS

Figure 4:
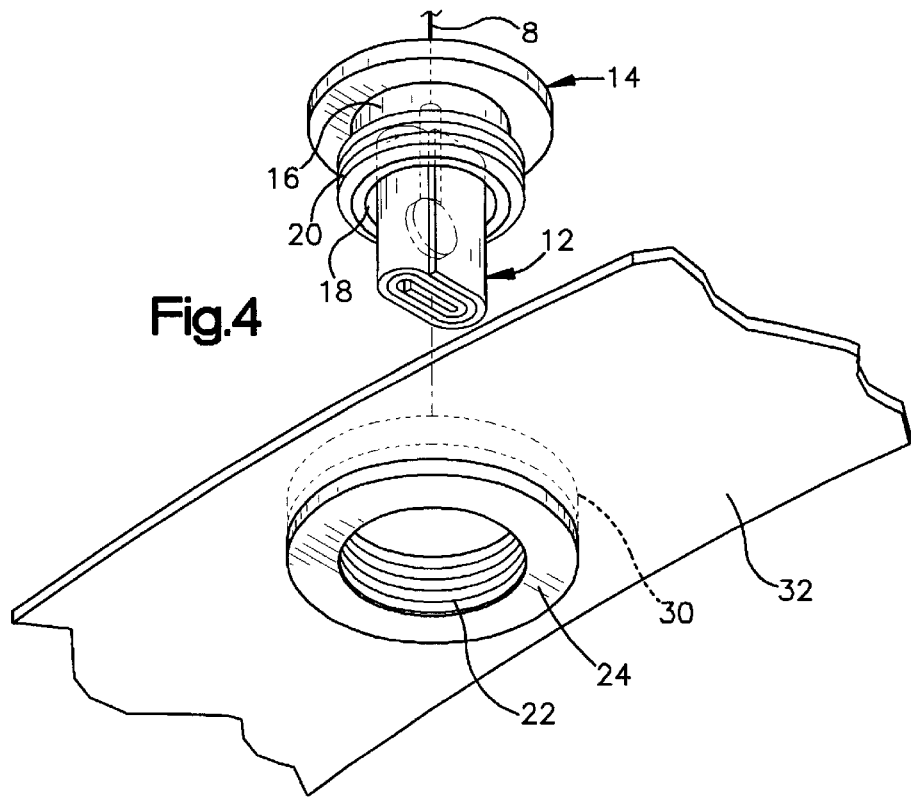
FIG. 4 is a perspective view of a wrapped electrode assembly and an electrode holder support structure of the invention.
Figure 5:
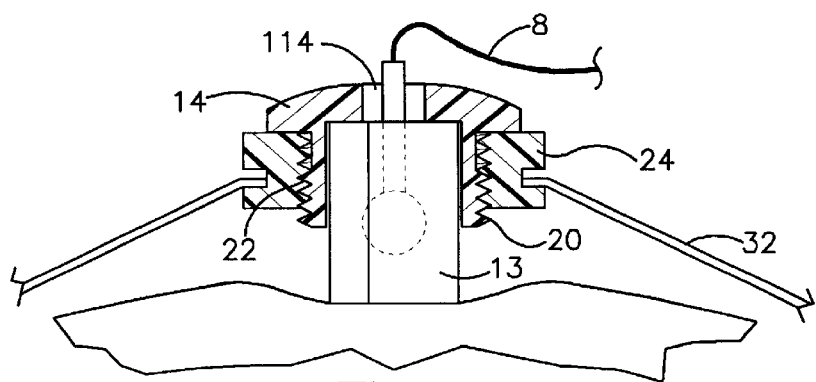
FIG. 5 is a cross-sectional view of an EEG electrode mounting assembly engaged in an electrode mounting structure within a band or strap attached to a head.

As shown in FIGS. 1–3, an electrode assembly, indicated generally at 1, is formed by an electrode 2, having a conductor 4, a connector 6 and a lead wire 8. The conductor 4 is preferably a metallic element which is gold plated. Lead wire 8 is connected to the signal input of any suitable brain wave monitoring equipment. The electrode 2 is wrapped or otherwise covered or substantially encapsulated or surrounded by an absorptive material 10, which is also preferably a flexible material. The absorptive material 10 is also referred to generally herein as the "electrode wrap 10". In one embodiment as shown, the electrode wrap 10 is in the form of a strip of flexible, absorptive material such as felt, which is rolled axially about the electrode 2, to form an electrode assembly 12 as shown in FIG. 3. The felt strip form is preferably dimensioned with a length of approximately 3" and a width of ¾". After the electrode wrap 10 is tightly wound or rolled about the electrode 2, it can be tack sewn in the configuration shown in FIG. 3. The material 10 such as felt is preferably of relatively high density which will maximize the amount of liquid which can be absorbed and retained.

In another form, the absorptive material or electrode wrap 10 may be a block or chunk of felt or other absorptive material with an interior cavity, such as a slit, in which the electrode 2 is inserted. In still another form, the electrode wrap 10 may be made of a material which is conductive without being saturated by a conductive liquid. Any flexible material with sufficient conductive properties and low impedance are useable, including fiber-based materials and polymers such as conductive rubber. The flexibility of the material provides a positive and live mechanical connection of the electrode to skin or the scalp, while the conductivity (created by the presence of a conductive fluid such as saline within the material) and low impedance provides an electrical connection to the electrode 2.

As shown in FIGS. 3–6, the electrode assembly 12 is fitted within an electrode holder 14. In one particular form as shown, a body portion 16 of the electrode holder 14 is a cylindrical plug having a cylindrical internal cavity 18 configured to receive and securely house the electrode assembly 12. Threads 20 are formed on an exterior of the body portion 16 of the electrode holder 14. Threads 20 are engaged with female threads 22 in a retainer ring 24. Of course, other engagement mechanisms between the electrode holder 14 and the retainer ring 24 can be employed. An end segment 13 of the electrode assembly 12 protrudes from the body portion 16 of the electrode holder 14, and remains so exposed when the electrode holder 14 is engaged in the retainer ring 24. Preferably, the end segment 13 of the electrode assembly 10 protrudes from the electrode holder 14 by approximately ⅜ of one inch.

The contact end 13 of the electrode assembly 12 serves as a flexible, dynamic electrode contact which establishes and maintains a secure electrical contact throughout a brain wave monitoring session. The electrode wrap 10 also acts as a sponge as installed, and can if necessary accept additional solution which can be applied by dropper or squeeze bottle to the individual electrode assemblies, through the opening 114 in the electrode holder 14, as illustrated in FIG. 7. The vertically oriented spiral wrap 10 is ideally suited to readily absorb additional electrolyte solution applied in this manner, and to transfer the solution to the opposite end of the electrode wrap 10, into contact with the scalp. The solution may also have cleaning or antibiotic qualities which are active at each electrode site. Also, excess or reserve solution can be wrung from the electrode wrap 10 by further tightening of the electrode holder 14 into the retaining ring 24, which compresses the electrode wrap 10 against the scalp. The conductivity of individual electrode sites can be monitored and the solution applied or adjusted where required.

When constructed of fibrous or absorptive material, the electrode wrap 10 is preferably saturated with a conductive solution prior to installation in the electrode holder 14. One suitable solution is a saline solution of one teaspoon of common salt in 4 ounces of water. The entire electrode wrap 10 is preferably soaked in the saline overnight, and also stored in saline when not in use to insure saturation. Less preferable but acceptable results can be achieved by dipping the electrode wrap 10 in saline solution, wringing out excess, and installing in the electrode holder 14.

The retainer rings 24 for each electrode site, are installed in openings 30 in positioning straps 32, an example of which is shown in FIG. 8, or in a cap 34 as shown in FIG. 9. Each opening can be provided with a permanently mounted retainer ring 24, whereby electrodes can be installed at selected locations or sites dependent upon the analysis to be performed. The application sites can be prepped by use of electrode prep gel or alcohol swab to clean and degrease the skin area. The straps or cap or other configured headgear is put on, and the electrode holders 14 installed in the retainer rings 24. At this point the electrode wraps 10 may be additionally moistened with solution applied by a squirt bottle. The wearer may feel slight wetness at the contact area which confirms good electrical contact. As mentioned, the electrode holder 14 can be additionally tightened within the retainer ring 24.

The electrode impedance can then be checked between two electrodes. Impedance should be well below 60 Kohms per pair, and will typically be around 40 Kohms or less. It may be necessary to wait up to one minute for the electrical contact with the skin to stabilize. As shown in FIG. 7, earclip or mastoid electrodes may be used in combination with one or more electrode assemblies 1.

Figure 6:
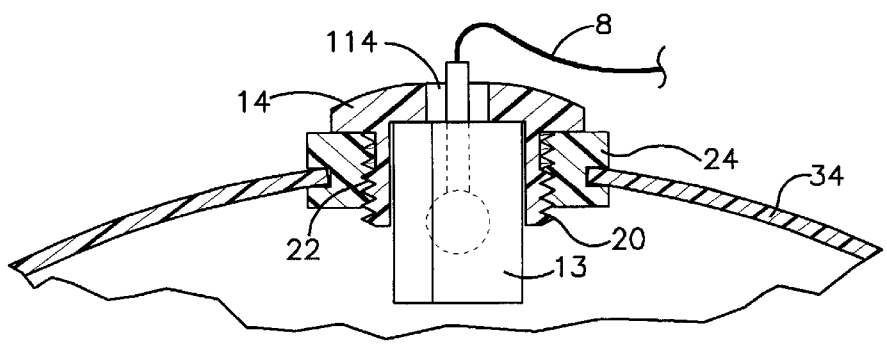
FIG. 6 is a cross-sectional view of an EEG electrode mounting assembly engaged in an electrode mounting structure within a mounting device.
Figure 10:
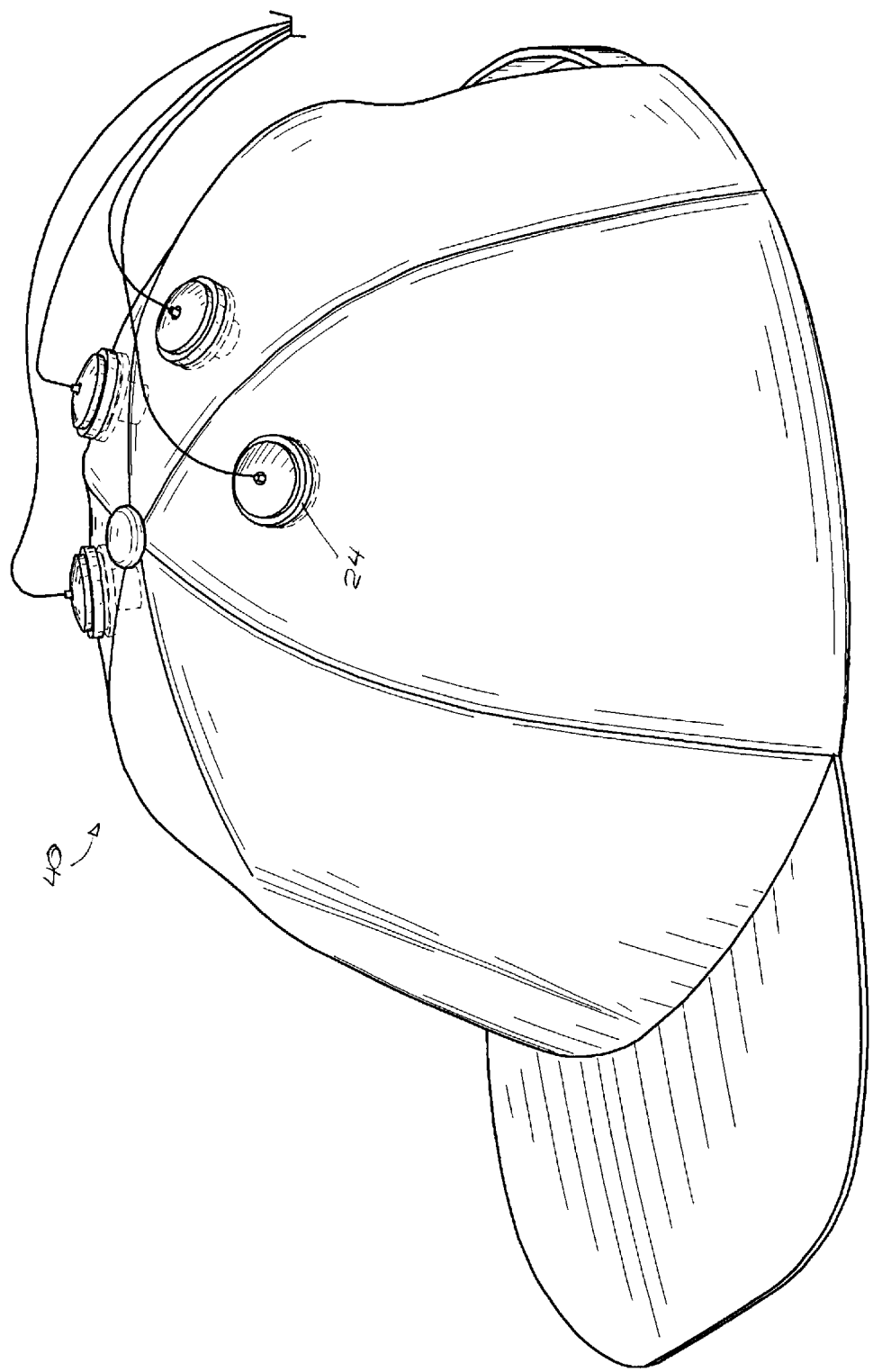
FIG. 10 is a perspective view of an EEG electrode mounting cap of the invention.

As shown in FIG. 10, the electrode assemblies 12 can be incorporated into a flexible mounting structure, such as a fabric-constructed hat 40. Retaining rings 24 are mounted within openings in the selected regions of the cap, with the perimeter of the openings fitting within the annular groove 25 in the retaining ring 24, as shown in FIG. 6. The perimeter of the openings in the cap are preferably reinforced with stitching or in the manner of a grommet to securely engage with the retaining ring 24. Particular advantages of the flexible mounting structure such as the fabric hat 40 as a positioning device for the electrodes is the predetermined positional array of electrodes according to established EEG practices, and near instantaneous connection of the electrodes to a scalp. In practice, the electrode wrap material 10 of each of the electrode assemblies 12 in the hat 40 are pre-wetted with the described solution, and the hat then placed securely on the subject's head. The hat design can of course be contoured to optimize the physical contact of the electrode assemblies with the scalp of the wearer. This includes both the overall shape of the portion of the hat which covers the scalp, and adjustment straps which can optimize the fit. Different hats with different numbers and location arrays of electrodes can be provided for different types of EEG analysis. Also, supplementary electronics, displays or headsets can be attached to or worn with the hat 40, or ear speakers incorporated into the structure of the hat.

After use, the electrode wraps 10 are removed from the holder 14, and can be either discarded, or disinfected by application of a disinfectant such as Hibistat, and stored in a saline solution which will prevent germs.

As thus described and practiced, the invention provides an improved system and method for quickly establishing positive EEG scalp leads. Any type of mounting device which holds the contact end 13 of the electrode assembly 1 against the scalp can be used to practice the invention. The size and density of the material of the electrode wrap 10 provides sufficient liquid volumetric capacity such that the electrode wrap 10 functions both as a mechanically dynamic electrical conductor, from the scalp to the electrode 4, and as a reservoir of the conductive medium such as the saline solution absorbed and held by the material. Any material or structure which performs this function in combination with an electrode, and any structure which holds or positions the combination of an electrode and a material surrounding the electrode, is within the scope of this invention.

What is claimed is:

1. An electrode assembly for establishing an electrical contact with a scalp, the electrode assembly comprising:

an electrode in a form of a conductive element attached to a lead;

an electrode wrap material substantially surrounding the electrode;

an electrode wrap holder having a cavity configured to accept and hold the electrode wrap material and the electrode substantially surrounded by the electrode wrap material, and to leave exposed a contact portion of the electrode wrap material for contact with the scalp, the electrode wrap holder being configured for attachment to an electrode positioning structure which positions an exposed contact portion of the electrode wrap material in contact with the scalp.

2. The electrode assembly of claim 1 wherein the electrode wrap material is a fabric material having a fibrous structure which absorbs liquid.

3. The electrode assembly of claim 2 wherein the electrode wrap material is felt.

4. The electrode assembly of claim 1 wherein the electrode wrap material is in the form of a strip of material which is rolled around the electrode.

5. The electrode assembly of claim 1 wherein the electrode wrap material is formed with an opening to receive and hold the electrode.

6. The electrode assembly of claim 1 wherein the electrode wrap holder is generally cylindrical, and has an internal cavity in which a portion of the electrode wrap material fits.

7. The electrode assembly of claim 1 wherein an exterior surface of the electrode wrap holder is configured for attachment to the electrode positioning structure.

8. The electrode assembly of claim 7 wherein the electrode wrap holder has threads on the exterior surface.

9. The electrode assembly of claim 1 in combination with a retainer ring configured for engagement with the electrode wrap holder.

10. The electrode assembly of claim 9 in combination with an electrode positioning device with which the retainer ring is engaged.

11. The electrode assembly of claim 1 in combination with a conductive liquid absorbed by and within the electrode wrap material.

12. The electrode assembly of claim 11 wherein the conductive liquid in the electrode wrap material is a saline solution.

13. The electrode assembly of claim 1 wherein a length of the electrode wrap material is greater than a length of an internal cavity of the electrode wrap holder, and a portion of the electrode wrap material extends out of the electrode wrap holder.

14. The electrode assembly of claim 1 wherein the electrode wrap material is substantially saturated with a conductive liquid.

15. The electrode assembly of claim 9 wherein a position of the retainer ring relative to the electrode wrap holder is adjustable when the electrode wrap holder and retainer ring are combined.

16. A wet EEG electrode system for providing one or more electrode contacts with a scalp for EEG analysis, the wet EEG electrode system comprising:

at least one electrode in contact with an electrode wrap, the electrode wrap being made of an absorptive material, and containing a conductive fluid;

the electrode wrap at least partially within an electrode wrap holder, with a contact portion of the electrode wrap extending from the electrode wrap holder;

the electrode wrap holder being configured for attachment to an electrode positioning device which holds the contact portion of the electrode wrap in contact with the scalp, whereby electrical signals from the scalp are conducted by the conductive fluid in the electrode wrap to the electrode in contact with the electrode wrap.

17. The wet EEG electrode system of claim 16 wherein the electrode wrap is made of felt.

18. The wet EEG electrode system of claim 16 wherein the electrode wrap is in a form of a strip of material which is wrapped around the electrode.

19. The wet EEG electrode system of claim 16 wherein the electrode wrap substantially surrounds the electrode.

20. The wet EEG electrode system of claim 16 wherein the electrode wrap is a non-fabric material which can hold liquid.

21. The wet EEG electrode system of claim 16 wherein the electrode wrap has a cavity for receiving and holding the electrode in electrically conductive contact with a liquid in the electrode wrap.

22. The wet EEG electrode system of claim 16 wherein the electrode wrap holder has a cavity for receiving the electrode wrap, and an external attachment structure for attachment to an electrode positioning device.

23. The wet EEG electrode system of claim 16 wherein the electrode wrap holder is generally cylindrical.

24. The wet EEG electrode system of claim 16 in combination with a retainer configured to be coupled with the electrode wrap holder, the retainer being attachable to an electrode positioning device.

25. The wet EEG electrode system of claim 24 in combination with the electrode positioning device in the form of a strap which fits on a head.

26. The wet EEG electrode system of claim 24 in combination with the electrode positioning device in the form of a cap which fits on a head.

27. The wet EEG electrode system of claim 16 wherein the electrode wrap extends out of a cavity in the electrode wrap holder.

28. The wet EEG electrode system of claim 27 wherein a lead from the electrode extends out of the cavity of the electrode wrap holder in a direction generally opposite to the contact portion of the electrode wrap which extends from the electrode wrap holder.

29. Electrode assembly for establishing electrically conductive contact with a scalp having an electrode in contact with an electrode wrap, the electrode wrap containing a conductive liquid and being held in contact with the scalp whereby electrical signals can be conducted from the scalp to the electrode by the conductive liquid in the electrode wrap.

30. The wet EEG system of claim 16 wherein the electrode wrap holder has an opening through which the conductive fluid can pass into contact with the electrode wrap in the electrode wrap holder.

31. A flexible EEG electrode mounting system for positioning a plurality of EEG electrodes against a scalp for EEG analysis, the flexible EEG electrode mounting system comprising:

a flexible EEG electrode mounting structure made of a flexible material dimensioned to substantially cover a scalp portion of person wearing the mounting structure;

openings in the mounting structure adapted to engage an electrode assembly, the electrode assembly comprising at least one EEG electrode substantially surrounded by an electrode wrap;

the electrode assembly engaged in each of the openings in the mounting structure, the electrode assembly being within a holder which is held in position within the opening by a retainer ring engaged with the opening, whereby a contact portion of the electrode assembly is held in an interior underside portion of the flexible mounting structure, and an electrical lead extends from the electrode assembly and an exterior topside portion of the flexible mounting structure.

32. The flexible EEG electrode of claim 31 wherein the electrode holder is in the form of a threaded plug which engages with the retainer ring.

\* \* \* \* \*